(12) United States Patent
Fu et al.

(10) Patent No.: US 9,314,503 B2
(45) Date of Patent: Apr. 19, 2016

(54) SUSTAINED RELEASE SYSTEMS AND PREPARATION METHOD THEREOF

(75) Inventors: Yin-Chin Fu, Kaohsiung (TW); Chih-Kuang Wang, Hsinchu (TW); Gwo-Jaw Wang, Kaohsiung (TW); Mei-Ling Ho, Kaohsiung (TW); Je-Ken Chang, Kaohsiung (TW); Cherng-Chyi Tzeng, Kaohsiung (TW)

(73) Assignee: KAOHSIUNG MEDICAL UNIVERSITY, Kaohsiung (TW)

( * ) Notice: Subject to any disclaimer, the term of this patent is extended or adjusted under 35 U.S.C. 154(b) by 1088 days.

(21) Appl. No.: 12/832,248

(22) Filed: Jul. 8, 2010

(65) Prior Publication Data
US 2011/0052691 A1 Mar. 3, 2011

Related U.S. Application Data (60) Provisional application No. 61/237,696, filed on Aug. 28, 2009.

(51) Int. Cl.
| | |
|---|---|
| *A61K 9/14* | (2006.01) |
| *A61K 38/18* | (2006.01) |
| *A61K 9/50* | (2006.01) |
| *A61K 38/29* | (2006.01) |
| *A61K 38/30* | (2006.01) |

(52) U.S. Cl.
CPC ............. *A61K 38/1875* (2013.01); *A61K 9/146* (2013.01); *A61K 9/5031* (2013.01); *A61K 38/1825* (2013.01); *A61K 38/1841* (2013.01); *A61K 38/1858* (2013.01); *A61K 38/29* (2013.01); *A61K 38/30* (2013.01)

(58) Field of Classification Search
None
See application file for complete search history.

(56) References Cited

PUBLICATIONS

Shim, I. et al., "Healing of articular cartilage defects treated with a novel drug-releasing rod-type implant after microfracture surgery", J. Controlled Release, Apr. 2008, vol. 129: pp. 187-191.*

* cited by examiner

*Primary Examiner* — Michael Burkhart
(74) *Attorney, Agent, or Firm* — WPAT, P.C.; Anthony King (57) ABSTRACT

The present invention relates to a hydrophilic drug and β-tricalcium phosphate (β-TCP) coating on a surface area of biopolymer matrix to form a sustained release system. The present invention also provides a method for preparing a sustained release system, comprising providing a surface are of biopolymer matrix coated with a hydrophilic drug and β-TCP.

10 Claims, 5 Drawing Sheets
(1 of 5 Drawing Sheet(s) Filed in Color)

×100 Optical microscope    500μm

3B

×100 Fluorescence microscope    500μm

Particle Size (μm)

Figure 5

SUSTAINED RELEASE SYSTEMS AND PREPARATION METHOD THEREOF

CROSS REFERENCE TO RELATED APPLICATIONS

The present invention claims priority to U.S. Provisional Patent Application No. 61/237,696, filed Aug. 28, 2009, which is incorporated herein by reference in its entirety.

FIELD OF THE INVENTION

The invention relates to a sustained release system, and more particularly to a sustained release system comprising a hydrophilic drug and β-tricalcium phosphate (β-TCP) coating on a surface area of biopolymer matrix and a preparation method thereof.

BACKGROUND OF THE INVENTION

Currently, sustained release systems are widely applied in various therapies, including surgical transplant, tissue regeneration or wound wrap therapies. Generally, drugs or bioactive substances are delivered to specific sites to cure various diseases using the sustained release systems. Specifically, the sustained release systems may deliver antibiotics to a specific site to prevent other sites from infection or combine with tissue regeneration engineering to provide essential growth factors.

Thus, development of safe sustained release systems with improved functions is desirable. For example, a sustained release system may be capable of generating high drug activity with minimal side effect. Biodegradable materials have been widely applied in sustained release systems because of their stable release rates and lack of toxicity. Common drugs used in sustained release systems include small molecules, peptides or proteins.

Common biodegradable materials are aliphatic polyesters include polylactic acid (PLA), polyglycolic acid (PGA), polylactic-co-glycolic acid (PLGA), polyanhydride or polycaprolactone (PCL). Such biodegradable materials can be shaped into various shapes. Specifically, for example, sponge, strip, fiber, colloid or microparticle (micrograin) shapes. As those skilled in the art know, the shape of a biodegradable material affects the physical properties of carried drugs when applied by an intramuscular injection or a subcutaneous injection. Biodegradable materials with microparticle shapes are popularly used because of their characteristics include: small size of about 0.1 to 500 μm, controlled release rate and their facilitation to inject directly to an organism. Thus, development of microparticle with small size and high entrapment efficiency is desirable.

Currently, processes for forming microparticles comprise emulsion solvent evaporation, phase separation, spray-drying, solvent extraction, atomization-freeze, salting out or nano-precipitation processes. For emulsion solvent evaporation, a hydrophobic polymer is dissolved in an organic solvent includes dichloromethane, chloroform or ethyl acetate, to form a polymer solution. A hydrophobic drug is then dissolved and suspended in the polymer solution. Second, the polymer solution is added to an aqueous solution containing a hydrophilic surfactant. After removal of solvent, a micrograined sustained release system is obtained. Even though the method of emulsion solvent evaporation is suitable for the use of hydrophobic drugs, it can not be applied to hydrophilic drugs.

The double emulsion method of water-in-oil-in-water (w/o/w) is suitable for the use of hydrophilic drugs. A biodegradable material and a hydrophobic surfactant are dissolved in an organic solvent to prepare a polymer solution. A hydrophilic drug solution is then emulsified with the polymer solution to form a w/o emulsion. The w/o emulsion is emulsified with an aqueous solution contains a hydrophilic surfactant to form a w/o/w double emulsion system. After removal of solvent, a micrograined sustained release system encapsulating hydrophilic drugs is obtained.

Additionally, a solid-in-oil-in-water (s/o/w) emulsion method has also been developed. A protein drug is lyophilized to form a solid. The solid protein drug is then encapsulated by the s/o/w phase. However, the activity of the protein drug will be decreased during the process of lyophilization because it is exposed in an organic solvent and has no protection. Also, the solid protein drug often does not uniformly disperse in the organic solvent with the s/o/w emulsion.

Thus, development of a preparation method or composition capable of protecting and effectively carrying a sensitive drug is desirable, particularly for susceptible hydrophilic drugs. The susceptible hydrophilic drugs include peptides, proteins or nucleic acid. However, when some biodegradable materials are hydrolyzed in an organism, its microenvironment pH value may be reduced, deteriorating cell growth. Thus, development of a sustained release system capable of protecting a drug, sustained release and effectively carrying drugs is essential.

Calcium phosphate ceramics such as hydroxyapatite and β-tricalcium phosphate (β-TCP) are used as bone substitute materials in the repair of bone defects. In particular, β-TCP is widely used in clinical orthopedic surgery due to its high osteoconductivity, easy manipulation, and a lack of histotoxicity. U.S. 6344209 disclosed a solid composition comprising a medicinal substance and an apatite-coated biodegradable polymer. It also disclosed a method for producing this solid composition by subjecting a substrate comprising a medicinal substance and a biodegradable polymer to immersion in an aqueous ion solution which is capable of forming an apatite. U.S. Patent Application 20090087472 relates to controlled release of biopharmaceutical growth factors from a hydroxyapatite coating on a bioresorbable substate used in orthopedic implant.

SUMMARY OF THE INVENTION

The present invention relates to a sustained release system, comprising a hydrophilic drug and β-tricalcium phosphate (β-TCP) coating on a surface area of biopolymer matrix. The present invention also relates to a method for preparing a sustained release system, comprising providing a surface area of biopolymer matrix coated with a hydrophilic drug and β-tricalcium phosphate (β-TCP).

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention can be more fully understood by reading the subsequent detailed description and examples with references made to the accompanying drawing.

FIG. 2B shows a diameter distribution of pure PLGA microparticles were made by w/o/w method according an embodiment of the invention.

FIG. 4B shows a diameter distribution of pure PLGA microparticles were made by sprayed dry according an embodiment of the invention.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

One embodiment of the invention provides a sustained release system comprising a hydrophilic drug and β-tricalcium phosphate (β-TCP) coating on a surface area of biopolymer matrix. The hydrophilic drug is small molecule, protein, nucleic acid, antibiotic or growth factor.

The surface area of biopolymer matrix of the sustained release system is phospholipids, lecithin, polylactic acid (PLA), polyglycolic acid (PGA), polylactic-co-glycolic acid (PLGA), polyglutamic acid (PGA), polycaprolactone (PCL), polyanhydrides, polyamino acid, polydioxanone, polyhydroxybutyrate, polyphophazenes, polyesterurethane, polycarbosyphenoxypropane-cosebacic acid or polyorthoester or a mixture thereof.

The hydrophilic drug of the sustained release system may comprise proteins such as peptides or enzymes, nucleic acid, antibiotics such as penicillin, cefazolin, vancomycin or lincomycin, growth factors such as BMPs, TGF-β1, fibroblast growth factors, platelet-derived growth factors, parathyroid hormone, parathyroid hormone derivatives or insulin-like growth factors, or hydrophilic compound drugs.

The surface area of biopolymer matrix of the sustained release system is in a form of microgranular, sponge, fiber or irregular shape. In one embodiment, the surface area of biopolymer matrix in a form of microgranular of the sustained release system has an average particle size of about 0.1-500 μm.

The present invention further provides a method for preparing a sustained release system, comprising providing a surface area of biopolymer matrix coated with a hydrophilic drug and β-tricalcium phosphate (β-TCP). The hydrophilic drug is small molecule, protein, nucleic acid, antibiotic or growth factor.

The surface area of biopolymer matrix of the method for preparing a sustained release system is phospholipids, lecithin, polylactic acid (PLA), polyglycolic acid (PGA), poly-lactic-co-glycolic acid (PLGA), polyglutamic acid (PGA), polycaprolactone (PCL), polyanhydrides, polyamino acid, polydioxanone, polyhydroxybutyrate, polyphophazenes, polyesterurethane, polycarbosyphenoxypropane-cosebacic acid or polyorthoester or a mixture thereof.

The hydrophilic drug of the method for preparing a sustained release system may comprise proteins such as peptides or enzymes, nucleic acid, antibiotics such as penicillin, cefazolin, vancomycin or lincomycin, growth factors such as BMPs, TGF-β1, fibroblast growth factors, platelet-derived growth factors, parathyroid hormone, parathyroid hormone derivatives or insulin-like growth factors, or hydrophilic compound drugs.

The surface area of biopolymer matrix of the method for preparing a sustained release system is in a form of sponge, microgranular, fiber or irregular shape. In one embodiment, the surface area of biopolymer matrix in a form microgranular of the sustained release system has an average particle size of about 0.1-500 μm.

The surface area of biopolymer matrix of the method for preparing a sustained release system is produced by spray-drying or a method of preparing water-in-oil-in-water (w/o/w), oil-in-water (o/w), solid-in-oil-in-water (s/o/w), electrospinning, lyophilization drying or other porous polymer fabrication method. The method of preparing water-in-oil-in-water (w/o/w) or oil-in-water (o/w) comprises mixing an organic solvent with a second aqueous solution containing a hydrophilic surfactant and the organic solvent is dichloromethane, chloroform, ethyl acetate (EA), 1,4-dioxane, N,N-dimethylformamide (DMF), dimethyl sulfoxide (DMSO), toluene or tetrahydrofuran (THF).

In one embodiment, the hydrophilic surfactant of the method of preparing water-in-oil-in-water (w/o/w) or oil-in-water (o/w) is polyvinyl alcohol (PVA), NP-5, Triton x-100, Tween 40, PEG 200, PEG 800, sodium dodecyl sulfate (SDS), alcohol ethoxylates, alkylphenol ethoxylates, secondary alcohol ethoxylates, fatty acid ester or alkyl polyglycosides.

The method for preparing a sustained release system of the present invention further comprises coating an excipient on the surface area of biopolymer matrix. The excipient of the present invention is sugar, dextrin, α,β-trehalose, D-(+)-trehalose, sucrose, glycerol, cyclodextrin, polyhydric alcohols, polyethylene glycol (PEG) or bovine serum protein (BSA).

EXAMPLE

Example 1

Preparation of the Controlled Release System (1) (Double Emulsion Method/Basic Substance/Hydrophilic Drug)

Figure 1:
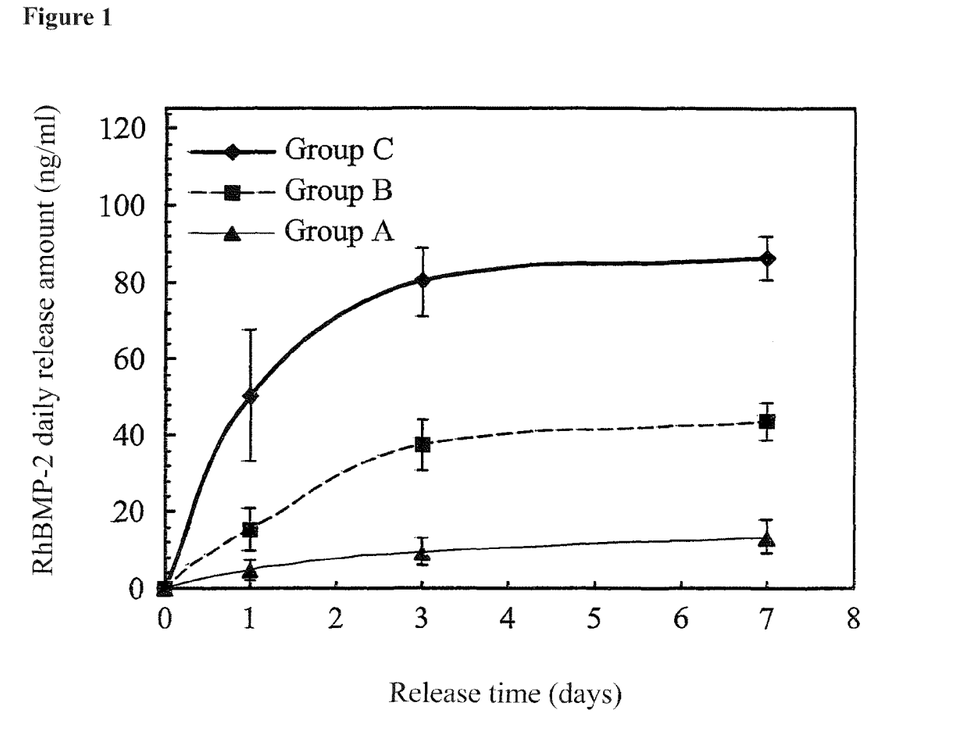
FIG. 1 shows release profiles of PLGA microparticles encapsulating HAp and rhBMP-2, coated with rhBMP-2 and coated with HAp and rhBMP-2 according an embodiment of the invention.

8 mg of hydroxyapatite (HAp) powder and 2,500 ng of recombinant human bone morphogenetic protein-2 (rhBMP-2) were added to 250 μl of a PBS buffer solution and shaken with a shaker for 5 minutes to form a first aqueous solution (rhBMP-2/HAp/PBS). 0.25 g of PLGA65/35 was dissolved in 2.5 ml of dichloromethane to form a 10% PLGA solution. The first aqueous solution (rhBMP-2/HAp/PBS) and the 10% PLGA solution were mixed and stirred at 1,000 rpm for 15 minutes to form a first emulsion (w/o). The first emulsion was added to 10 ml of a 0.1% (w/v) polyvinyl alcohol (PVA) second aqueous solution and stirred at 500 rpm for 5 minutes to form a second emulsion (w/o/w). The second emulsion was continuously stirred for 4 hours and then left standing for one minute. An upper layer thereof was collected. A centrifugal lower layer was collected by centrifugation of the upper layer at 3,000 rpm for 5 minutes. The original and centrifugal lower layers were washed with 10 ml of secondary water for one minute. After centrifugation and washing twice, a new centrifugal lower layer was collected and lyophilized to form PLGA microparticles encapsulating HAp and rhBMP-2. The release profile of the PLGA microparticles encapsulating HAp and rhBMP-2 is shown in FIG. 1 (Group A). The burst release of the rhBMP-2 was effectively reduced by the HAp. Results from an ELISA kit showed that an extremely small amount of rhBMP-2 was completely entrapped by the PLGA microparticles and the rhBMP-2 had a low release rate (1~2 ng/day), for less than 7 days. However, following 7 days, the rhBMP-2, was still continuously released.

Example 2

Preparation of the Controlled Release System (2) (Double Emulsion Method/Coating/Hydrophilic Drug)

250 μl of a PBS buffer solution was shaken with a shaker for 5 minutes to form a PBS first aqueous solution. 0.25 g of PLGA65/35 was dissolved in 2.5 ml of dichloromethane to form a 10% PLGA solution. The PBS first aqueous solution and the 10% PLGA solution were mixed and stirred at 1,000 rpm for 15 minutes to form a first emulsion (w/o). The first emulsion was added to 10 ml of a 0.1% (w/v) polyvinyl alcohol (PVA) second aqueous solution and stirred at 500 rpm for 5 minutes to form a second emulsion (w/o/w). The second emulsion was continuously stirred for 4 hours and then left standing for one minute. An upper layer thereof was collected. A centrifugal lower layer was collected by centrifugation of the upper layer at 3,000 rpm for 5 minutes. The original and centrifugal lower layers were washed with 10 ml of secondary water for one minute. After centrifugation and washing twice, a new centrifugal lower layer was collected and lyophilized to form PLGA microparticles. An aqueous solution containing 1,000 ng of rhBMP-2 was then coated on the surface of the PLGA microparticles. The release profile of the PLGA microparticles coated with rhBMP-2 is shown in FIG. 1 (Group B). Recombinant human bone morphogenetic protein-2 (rhBMP-2) physically adsorbed on the surface of the PLGA microparticles was shown to continuously release therefrom to an in-vitro solution via diffusion. Results from an ELISA kit showed that the release rate of the rhBMP-2 was high (10-18 ng/day) during the first three days and then achieved a stable sustained-release condition (1-3 ng/day) thereafter.

Example 3

Preparation of the Controlled Release System (3) (Double Emulsion Method/Coating/Basic Substance/Hydrophilic Drug)

250 μl of a PBS buffer solution was shaken with a shaker for 5 minutes to form a PBS first aqueous solution. 0.25 g of PLGA65/35 was dissolved in 2.5 ml of dichloromethane to form a 10% PLGA solution. The PBS first aqueous solution and the 10% PLGA solution were mixed and stirred at 1,000 rpm for 15 minutes to form a first emulsion (w/o). The first emulsion was added to 10 ml of a 0.1% (w/v) polyvinyl alcohol (PVA) second aqueous solution and stirred at 500 rpm for 5 minutes to form a second emulsion (w/o/w). The second emulsion was continuously stirred for 4 hours and then left standing for one minute. An upper layer thereof was collected. A centrifugal lower layer was collected by centrifugation of the upper layer at 3,000 rpm for 5 minutes. The original and centrifugal lower layers were washed with 10 ml of secondary water for one minute. After centrifugation and washing twice, a new centrifugal lower layer was collected and lyophilized to form PLGA microparticles. An aqueous solution containing 2 mg of hydroxyapatite (HAp) powder and 2,000 ng of recombinant human bone morphogenetic protein-2 (rhBMP-2) was then coated on the surface of the PLGA microparticles. The release profile of the PLGA microparticles coated with HAp and rhBMP-2 is shown in FIG. 1 (Group C). Recombinant human bone morphogenetic protein-2 (rhBMP-2) physically adsorbed on the surface of the PLGA microparticles was shown to continuously release therefrom to an in-vitro solution via diffusion and PLGA hydrolysis. Results from an ELISA kit showed that the release rate of the rhBMP-2 was high (20-50 ng/day) during the first three days and then achieved a stable sustained-release condition (1-3 ng/day).

While the invention has been described by way of example and in terms of preferred embodiment, it is to be understood that the invention is not limited thereto. To the contrary, it is intended to cover various modifications and similar arrangements (as would be apparent to those skilled in the art). Therefore, the scope of the appended claims should be accorded the broadest interpretation so as to encompass all such modifications and similar arrangements.

Example 4

Morphology and Diameter Analysis of the Controlled Release System (Double Emulsion Method/Basic Substance)

Figures 2, 2A:
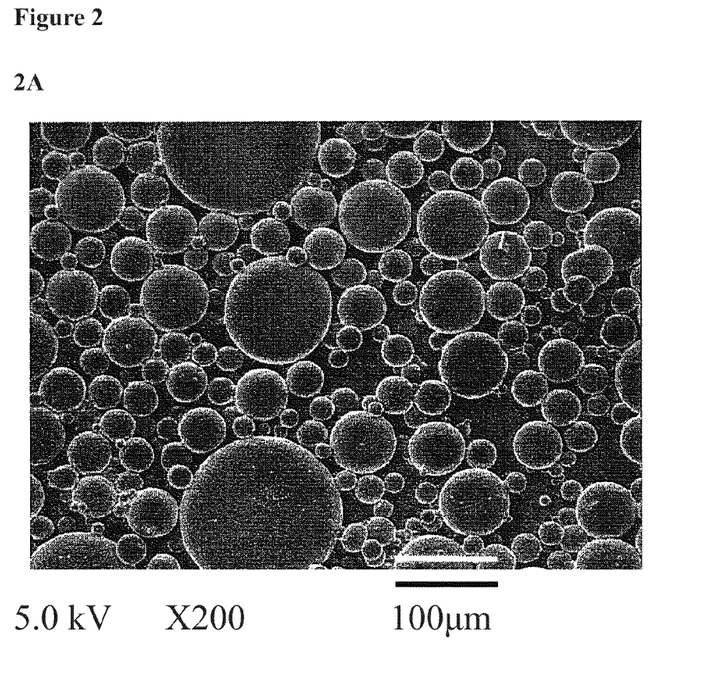
FIG. 2A shows morphology of pure PLGA microparticles were made by w/o/w method under an electron microscope according an embodiment of the invention.

A proper amount of PLGA50/50 and 0.2 wt % span 83 (surfactant) were dissolved in dichloromethane to form a 10% oil phase solution. PBS buffer solution were mixed to form a water phase. The water phase was then added to the oil phase solution and emulsified with a Vortex mixer to form an emulsion. After removal of dichloromethane from the emulsion by extraction, PLGA microparticles were obtained. FIGS. 2A and 2B show morphology and a diameter distribution of the PLGA microparticles under an electron microscope. The PLGA microparticles were globular and had the diameter distribution ranging from 20 to 70 μm.

Example 5

Preparation, Entrapment Efficiency and Diameter Analysis of the Controlled Release System (5) (Single Emulsion Method)

Figures 3, 3A:
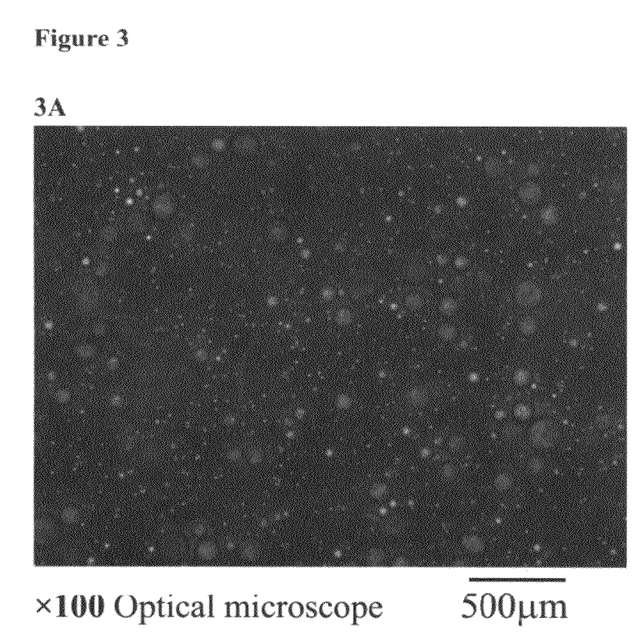
FIG. 3 shows morphology of the PLGA microparticles under an optic microscope (A) and fluorescent microscope (B).

0.5 ml of methanol and 84.2 mg of PLGA dissolved in 2.0 ml of dichloromethane were mixed and shaken with an ultrasonic shaker for 10 minutes to form a uniform organic solution (oil phase). 10 ml of a 0.1% polyvinyl alcohol (PVA) aqueous solution (water phase) was prepared. The oil phase was slowly dropped into the water phase containing the 0.1% polyvinyl alcohol (PVA) deionized aqueous solution under an ice bath with a stirrer at 800 rpm to respectively form various emulsions with oil/water ratios of 1:5, 1:8 and 1:10. After one hour, the ice bath was removed. The emulsions were stirred for 24 hours at room temperature to evaporate solvent therein. Solidified PLGA microparticles were then formed. The entrapment efficiency of the PLGA microparticles was 97%. Two apparent diameter distribution peaks respectively ranging from 100 nm to 400 nm and from 900 nm to 2,000 nm of the PLGA microparticles appeared. FIG. 3(A) (B) shows morphology of the PLGA microparticles under an optic microscope and fluorescent microscope. An optimal resolution was obtained using a green light source due to light emission from the hydrophobic fluorescent drug. Table 1 shows various oil/water ratio results for PLGA microparticles with various diameters. When the oil/water ratio was 1:5, the average diameter was 412 nm; when the oil/water ratio was 1:8, the average diameter was 379 nm; and when the oil/water ratio was 1:10, the average diameter was 282 nm.

TABLE 1 the relationship between oil/water ratio and diameter for PLGA microparticles

| Water/oil ratio | Diameter (nm) |
| --- | --- |
| 1:5 | 412 ± 85 |
| 1:8 | 379.6 ± 109.6 |
| 1:10 | 282.8 ± 70.6 |

Example 6

Preparation, Morphology and Diameter Analysis of the Controlled Release System (6) (Spray Drying Method/Basic Substance)

Figures 4, 4A:
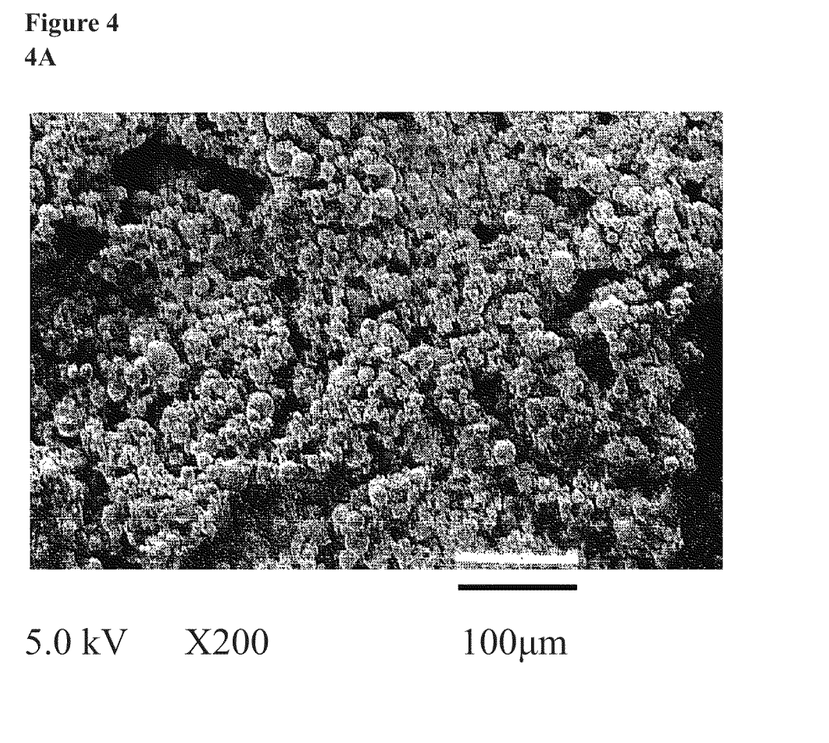
FIG. 4A shows morphology of pure PLGA microparticles were made by sprayed dry method under an electron microscope according an embodiment of the invention.

2 g of PLGA was dissolved in 20 ml of dichloromethane (DCM) to form a 10% PLGA/DCM solution. Hydroxyapatite (HAp) powder was dispersed in water to form an aqueous solution. The aqueous solution was then mixed with the PLGA/DCM/SIM solution and stirred with a magnetic stirrer for 30 minutes to form an emulsion. Next, the emulsion was fed into a granular machine to perform a spray granulation process to form PLGA microparticles. The conditions of the spray granulation process are shown in Table 2. FIGS. 4A and 4B show morphology and a diameter distribution of the PLGA microparticles under an electron microscope. The PLGA microparticles were globular and had the diameter distribution ranging from 10 to 30 μm. However, following detection by a DLS, it was shown that the diameter distribution thereof was from 10 to 100 μm due to the aggregation effect after spray granulation.

TABLE 2 the conditions of spray granulation process

| Inlet temperature (° C.) | 60 |
| --- | --- |
| Outlet temperature (° C.) | 50 |
| Feed rate (g/min) | 2.5 |
| Spray pressure (kgf/cm2) | 5 |

Example 7

Preparation of the Controlled Release System (2) (Double Emulsion Method/Coating/Hydrophilic Drug)

250 μl of a PBS buffer solution was shaken with a shaker for 5 minutes to form a PBS first aqueous solution. 0.25 g of PLGA65/35 was dissolved in 2.5 ml of dichloromethane to form a 10% PLGA solution. The PBS first aqueous solution and the 10% PLGA solution were mixed and stirred at 1,000 rpm for 15 minutes to form a first emulsion (w/o). The first emulsion was added to 30 ml of a 0.1% (w/v) polyvinyl alcohol (PVA) second aqueous solution and stirred at 600 rpm to form a second emulsion (w/o/w). The second emulsion was continuously stirred for 4 hours and then left standing for one minute. An upper layer thereof was collected. A centrifugal lower layer was collected by centrifugation of the upper layer at 3,000 rpm for 5 minutes. The original and centrifugal lower layers were washed with 10 ml of secondary water for one minute. After centrifugation and washing twice, a new centrifugal lower layer was collected and lyophilized to form PLGA microparticles. An aqueous solution containing 1,000 ng of rhBMP-2 was mixed with 2 mg Hydroxyapatite (HAp), 2, 4, 6 mg β-Tricalcium Phosphate (β-TCP) respectively and was then coated on the surface of the PLGA microparticles. The PLGA microparticles were freeze dried to from the final product.

Figure 5:
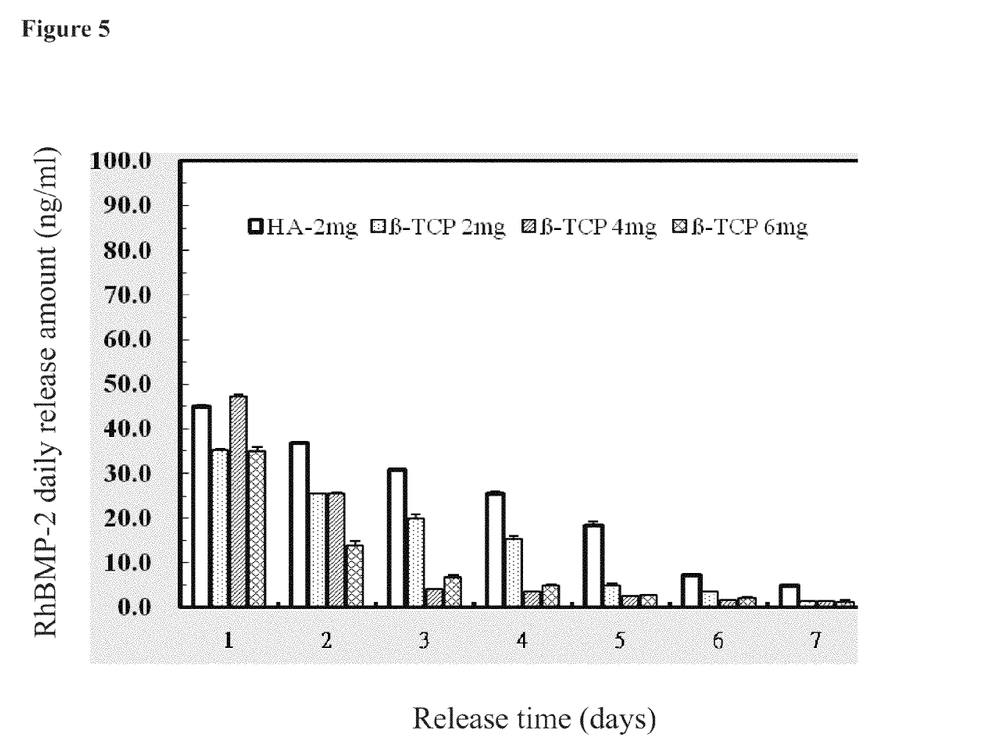
FIG. 5 shows the release profiles of rhBMP-2 activity for four kinds of samples (50 mg) in PBS by ELISA detection. Sample 1: 1000 ng rhBMP-2 with 2 mg HAp coating on PLGA microspheres; sample 2: 1000 ng rhBMP-2 with 2 mg β-TCP coating on PLGA microspheres; sample 3: 1000 ng rhBMP-2 with 4 mg β-TCP coating on PLGA microspheres; sample 4: 1000 ng rhBMP-2 with 6 mg β-TCP coating on PLGA microspheres.

The release profile of the PLGA microparticles coated with rhBMP-2, HAp and β-TCP is shown in FIG. 5. 50 mg microsphere rhBMP-2 compound was added into 5 ml PBS buffer to release. The HAp+rhBMP-2 or β-TCP+rhBMP-2 physically adsorbed on the surface of the PLGA microparticles was shown to continuously release therefrom to an in-vitro solution via diffusion.

Results from an ELISA kit showed that the release rate of the 2 mg HAp+rhBMP-2 was high (20-45 ng/day) during the first 5 days and then achieved a stable sustained-release condition (10-3 ng/day) thereafter; the release rate of the 2 mg β-TCP+rhBMP-2 was high (20-35 ng/day) during the first 4 days and then achieved a stable sustained-release condition (7-1 ng/day) thereafter; the release rate of the 4 mg β-TCP+rhBMP-2 was high (25-48 ng/day) during the first 2 days and then achieved a stable sustained-release condition (5-1 ng/day) thereafter; the release rate of the 6 mg β-TCP+rhBMP-2 was high (35 ng/day) at the first day and then achieved a stable sustained-release condition (15-1 ng/day) thereafter.

What is claimed is:

1. A sustained release system, comprising a hydrophilic drug and a β-tricalcium phosphate (β-TCP), wherein both the hydrophilic drug and the β-TCP are coated on a surface area of a biopolymer matrix, wherein the biopolymer matrix is selected from the group consisting of a polylactic acid (PLA), a polyglycolic acid (PGA) and a polylactic-co-glycolic acid (PLGA), wherein the surface area of the biopolymer matrix is in a form of a microgranular sponge, a fiber or an irregular shape.

2. The sustained release system of claim 1, wherein the hydrophilic drug is a small molecule, a protein, a nucleic acid, an antibiotic or a growth factor.

3. A method for preparing a sustained release system, comprising:
   (a) providing a biopolymer matrix with a surface area in a form of a microgranular sponge, a fiber or an irregular shape; and
   (b) coating both a hydrophilic drug and a β-tricalcium phosphate (β-TCP) on the surface area of the biopolymer matrix,
   wherein the biopolymer matrix is selected from the group consisting of a polylactic acid (PLA), a polyglycolic acid (PGA) and a polylactic-co-glycolic acid (PLGA).

4. The method of claim 3, wherein the hydrophilic drug is a small molecule, a protein, a nucleic acid, an antibiotic or a growth factor.

5. The method of claim 3, wherein the surface area of the biopolymer matrix is produced by spray-drying or a method of preparing water-in-oil-in-water (w/o/w), oil-in-water (o/w), solid-in-oil-in-water (s/o/w), electro-spinning, or lyophilization drying.

6. The method of claim 5, wherein the method of preparing water-in-oil-in-water (w/o/w) or oil-in-water (o/w) comprises mixing an organic solvent with a second aqueous solution containing a hydrophilic surfactant.

7. The method of claim 6, wherein the organic solvent is a dichloromethane, a chloroform, an ethyl acetate (EA), a 1,4-dioxane, a N,N-dimethylformamide (DMF), a dimethyl sulfoxide (DMSO), a toluene or a tetrahydrofuran (THF).

8. The method of claim 6, wherein the hydrophilic surfactant is a polyvinyl alcohol (PVA), a NP-5, a Triton x-100, a Tween 40, a PEG 200, a PEG 800, a sodium dodecyl sulfate (SDS), alcohol ethoxylates, alkylphenol ethoxylates, secondary alcohol ethoxylates, a fatty acid ester or alkyl polyglycosides.

9. The method of claim 3, further comprising coating an excipient on the surface area of the biopolymer matrix.

10. The method of claim 9, wherein the excipient is a sugar, a dextrin, a $\alpha,\beta$-trehalose, a D-(+)-trehalose, a sucrose, a glycerol, a cyclodextrin, polyhydric alcohols, a polyethylene glycol (PEG) or a bovine serum protein (BSA).

\* \* \* \* \*